United States Patent [19]

Carlson et al.

[11] 4,112,105

[45] Sep. 5, 1978

[54] ANTI-INFLAMMATORY 3-(SUBSTITUTED-AMINO)-2,1-BENZISO-THIAZOLES

[75] Inventors: John Alan Carlson, Nassau; Malcolm Rice Bell, East Greenbush, both of N.Y.

[73] Assignee: Sterling Drug Inc., New York, N.Y.

[21] Appl. No.: 793,629

[22] Filed: May 4, 1977

[51] Int. Cl.² .................. A61K 31/425; C07D 275/04
[52] U.S. Cl. ............................ 424/270; 260/293.57; 260/304 A; 260/551 S; 424/250; 424/267; 544/368; 544/391
[58] Field of Search ....... 260/304 A, 268 BC, 293.57; 424/270, 250, 267

[56] References Cited

U.S. PATENT DOCUMENTS

| 3,187,001 | 1/1965 | Meyer et al. | 260/304 A |
| 3,787,572 | 1/1974 | Boshagen et al. | 260/304 A |

Primary Examiner—Paul M. Coughlan, Jr.
Attorney, Agent, or Firm—Paul E. Dupont; B. Woodrow Wyatt

[57] ABSTRACT

3-(Substituted-amino)-2,1,-benzisothiazoles useful as anti-inflammatory agents are prepared by reductive cyclization of appropriately substituted 2-nitrothiobenzamides or by reaction of 3-chloro-2,1-benzisothiazoles with suitably substituted amines.

28 Claims, No Drawings

ANTI-INFLAMMATORY 3-(SUBSTITUTED-AMINO)-2,1-BENZISO-THIAZOLES

BACKGROUND OF THE INVENTION

1. Field of the Invention

The present invention relates to compositions of matter classified in the art of chemistry as 3-(substituted-amino)-2,1-benzisothiazoles, to processes and intermediates for the preparation thereof, and to a method of using the same for treating inflammation in mammals.

2. Prior Art

T. Onaka et al., Itsuu Kenkyusho Nempo 16, 53–63 (1971); Chemical Abstracts 77, 48,320w (1972) disclose the compounds:

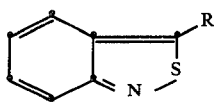

wherein:

R is $-NHCH_2CH_2N(C_2H_5)_2$ or

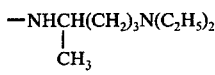

No pharmacological utility is disclosed for the compounds.

R. F. Meyer et al., J. Med. Chem. 8, 515–519 (1965) disclose in most pertinent part the compounds:

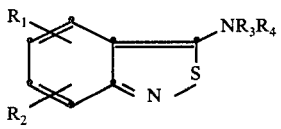

wherein inter alia:

$R_1$ is hydrogen;

$R_2$ is chloro, bromo or methoxy; and $R_3$ and $R_4$ are independently hydrogen, lower alkyl or phenyl.

Certain independent members of the series are stated to possess gastric antisecretory, antibradykinin, antinociceptive and mild antierythema activity.

Also disclosed are the intermediates

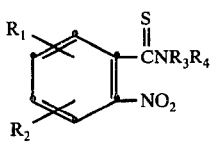

wherein $R_1$, $R_2$, $R_3$ and $R_4$ have the above-indicated meanings.

R. K. Richards et al. U.S. Pat. No. 3,170,955 patented Feb. 23, 1965 discloses the compounds:

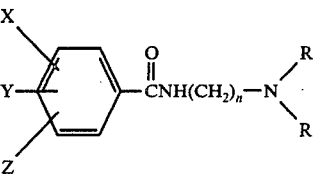

wherein:

X is halogen;

Y is amino or nitro;

Z is halogen or hydrogen;

n is a small whole number; and

R is lower alkyl.

The compounds are stated to have utility as antifibrillatory and anti-emetic agents.

SUMMARY OF INVENTION

The present invention provides novel, theraputically useful compounds which have been found to have anti-inflammatory activity and which are accordingly indicated for use as anti-inflammatory agents. Thus, the present invention relates to a group of novel $(X)_n$-substituted-3-$R_1R_2$N-2,1-benzisothiazoles which are useful as anti-inflammatory agents and to pharmaceutical compositions containing them.

It has also been discovered that the known 3-[4-(diethylamino)-1-methylbutylamino]-2,1-benzisothiazole has useful anti-inflammatory activity.

The invention also provides a group of $(X)_n$-substituted-N-$R_1$-N-$R_2$-2-nitrothiobenzamides which are useful as anti-inflammatory agents and also as intermediates in the preparation of certain $(X)_n$-substituted-3-$R_1R_2$N-2,1-benzisothiazoles.

In a method aspect the invention provides a method of reducing inflammation in a mammal in need of such treatment which comprises administering to said mammal an effective anti-inflammatory amount of a $(X)_n$-substituted-3-$R_1R_2$N-2,1-benzisothiazole.

The invention further provides a method of reducing inflammation in a mammal in need of such treatment which comprises administering to said mammal an effective anti-inflammatory amount of 3-[4-(diethylamino)-1-methylbutylamino]-2,1-benzisothiazole.

In one of its process aspects the invention relates to a process for preparing $(X)_n$-substituted-3-$R_1R_2$N-2,1-benzisothiazoles which comprises reductive cyclization of certain $(X)_n$-substituted-N-$R_1$-N-$R_2$-2-nitrothiobenzamides.

In a further process aspect the invention provides a process for preparing $(X)_n$-substituted-3-$R_1R_2$N-2,1-benzisothiazoles which comprises reacting $(X)_n$-substituted-3-chloro-2,1-benzisothiazoles with certain mono-and di-substituted amines.

DETAILED DESCRIPTION INCLUDING PREFERRED EMBODIMENTS

More specifically the invention sought to be patented resides, in a composition of matter aspect, in a compound having formula I hereinbelow:

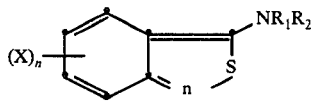

I wherein:
$R_1$ is hydrogen, methyl or ethyl;
$R_2$ is selected from the group consisting of

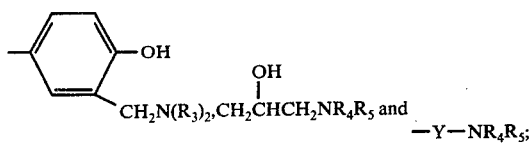
$$-Y-NR_4R_5;$$

or $R_1$ and $R_2$ taken together with the nitrogen atom are piperazinyl, N-lower alkylpiperazinyl or N-phenylpiperazinyl;
$R_3$ is methyl or ethyl;
$R_4$ and $R_5$ are the same or different and are selected from the group consisting of hydrogen, lower alkyl and hydroxy-lower alkyl; or
$R_4$ and $R_5$ taken together with the nitrogen atom are pyrrolidino, piperidino, hexamethyleneimino, piperazinyl, N-lower alkylpiperazinyl or N-phenylpiperazinyl;
Y is an alkylene group containing from 2 to 8 carbon atoms and separating the two nitrogen atoms by at least 2 carbon atoms;
X occupies any of positions 4,5,6, or 7 and is selected from the group consisting of methoxy and halo; and
$n$ is 1 or 2; or 0,1 or 2 when $R_2$ is

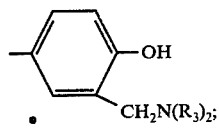

or an acid-addition salt thereof.

The compounds are useful as anti-inflammatory agents.

Preferred compounds of formula I are those wherein X is chloro; $n$ is 1; $R_1$ is hydrogen; and $R_2$ is $Y-NR_4R_5$ in which $R_4$ and $R_5$ are the same or different and are selected from the group consisting of lower alkyl and hydroxy-lower alkyl; and Y has the above-given meaning.

A particularly preferred species of formula I is 6-chloro-3-[4-(diethylamino)-1-methyl-butylamino]-2,1-benzisothiazole, i.e. the compound of formula I wherein X is chloro and occupies the 6-position; $n$ is 1; $R_1$ is hydrogen and $R_2$ is 4-(diethylamino)-1-methylbutyl. This compound exhibits low toxicity and a high degree of anti-inflammatory activity in both the carrageenin edema and adjuvant arthritis assays.

In another composition of matter aspect the invention sought to be patented residues in a compound selected from the group consisting of:

4-chloro-N-[4-(diethylamino)-1-methylbutyl]-2-nitrobenzamide,
4-chloro-N-[4-(diethylamino)-1-methylbutyl]-2-nitrothiobenzamide,
1-(4-chloro-2-nitrothiobenzoyl)-4-methylpiperazine,
4-chloro-N-[2-(dimethylamino)ethyl]-2-nitrothiobenzamide,
4-chloro-N-[3-(dimethylamino)propyl]-2-nitrothiobenzamide and
4-chloro-N-[4-(dimethylamino)butyl]-2-nitrothiobenzamide.

These compounds are useful as intermediates in the preparation of the compounds of formula I and also have utility per se as anti-inflammatory agents.

In a further composition of matter aspect, the invention sought to be patented resides in a pharmaceutical composition for the treatment of inflammation in mammals which comprises from about 25 to 500 mg. of a compound having formula I and a pharmaceutically acceptable carrier.

In a method aspect, the invention sought to be patented resides in the method of reducing inflammation in a mammal in need of such treatment which comprises administering to said mammal an effective anti-inflammatory amount of a compound having formula I.

In another method aspect the invention sought to be patented resides in the method of reducing inflammation in a mammal in need of such treatment which comprises administering to said mammal an effective anti-inflammatory amount of 3-[4-(diethylamino)-1-methylbutylamino]-2,1-benzisothiazole.

The invention sought to be patented resides in a process aspect, in a process for preparing a compound of formula I which comprises reductively cyclizing a 2-nitrothiobenzamide having formula II hereinbelow:

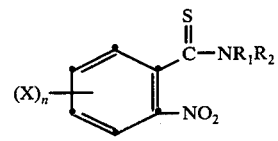

wherein:
X, $n$, $R_1$ and $R_2$ have the previously indicated meanings.

In another process aspect the invention sought to be patented resides in a process for preparing a compound of formula I which comprises reacting a 3-chloro-2,1-benzisothiazole having formula III hereinbelow:

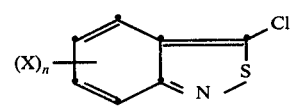

with an amine of formula IV hereinbelow:

$$R_1R_2NH \qquad (IV)$$

wherein in formulas III and IV, X, $n$, $R_1$ and $R_2$ have the above-given meanings.

When $R_2$ in the formulas herein is $-Y-NR_4R_5$, the alkylene group Y is a bivalent saturated aliphatic hydrocarbon radical containing from 2 to 8 carbon atoms arranged in a straight or in a branched chain and separating the two nitrogen atoms by at least 2 carbon atoms. The alkylene groups which are numbered beginning with the carbon atom bonded to the nitrogen at the 3-positions of the 2,1-benzisothiazole ring include 1,2-ethylene, 1,3-propylene, 1,4-butylene, 1,5-pentylene, 1,6-hexylene, 1-7-heptylene, 1,8-octylene, 2-methyl-1,2-ethylene, 1-methyl-1,3-propylene, 1-methyl-1,4-butylene, 3-methyl-1,5-pentylene, 2-ethyl-1,4-butylene, 3-methyl-1,6-hexylene, 2,4-dimethyl-1,5-pentylene, 1-methyl-2-ethyl-1,4-butylene, 1-methyl-1,7-heptylene, 3-ethyl-1,6-hexylene, 3-propyl-1,5-pentylene and the like.

It will be appreciated that when Y contains 2 carbon atoms the latter must, of course, be arranged in a straight chain; and similarly when Y contains 8 carbon atoms and separates the two nitrogen atoms by 8 carbon atoms, said carbon atoms must also be arranged in a straight chain. In all other instances Y can be either straight or branched.

The term "lower alkyl", as used herein, is intended to include monovalent saturated hydrocarbon radicals containing from 1 to 4 carbon atoms such as methyl, ethyl, n-propyl, iso-propyl, n-butyl, isobutyl, tert-butyl and sec-butyl.

When $R_4$ or $R_5$ in the formulas herein is hydroxy-lower alkyl there are included 2-hydroxyethyl, 2-hydroxypropyl, 3-hydroxypropyl, 1-hydroxy-2-propyl, 2-hydroxybutyl, 3-hydroxy-butyl, 4-hydroxybutyl, 1-hydroxy-2-butyl, 3-hydroxy-2-butyl, 4-hydroxy-2-butyl, 2-hydroxy-2-methylpropyl, 3-hydroxy-2-methylpropyl and 2-hydroxy-2,2-dimethylethyl.

It is of course well known that compounds containing a hydroxyl group and an amino group on the same carbon atom are generally unstable. Accordingly it will be appreciated that in the above-named hydroxy-lower alkyl groups the hydroxyl group and the nitrogen atom must be separated by at least 2 carbon atoms in order to provide a stable structure.

As used herein the term "halogen" includes, fluoro, chloro, bromo and iodo.

In accordance with one of the process aspects of the invention the 2,1-benzisothiazoles having formula I hereinabove are obtained by concomitant reduction and ring closure of the 2-nitrothiobenzamides of formula II. The reaction is conveniently effected with an appropriate reducing agent, for example stannous chloride, in an acidic medium such as hydrochloric acid, and is ordinarily carried out below room temperature, preferably at about 0°–10° C.

The 2-nitrothiobenzamides of formula II hereinabove are obtained from the corresponding 2-nitrobenzamides by reacting the latter with phosphorus pentasulfide in a suitable solvent such as 1,2-dichloroethane, chloroform or benzene at about 60°–100° C., preferably at the reflux temperature of the solvent.

The 2-nitrobenzamides in turn are obtained by reacting an amine of formula IV hereinabove with an appropriate 2-nitrobenzoyl chloride or bromide of formula V hereinbelow:

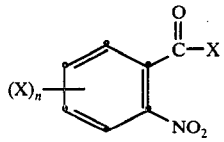

wherein X is chloro or bromo, according to conventional acylation procedures. Thus the amine (formula IV) is reacted with the 2-nitrobenzoyl halide (formula V) at about 0°–50° C. in an inert solvent such as chloroform, 1,2-dichloroethane or benzene in the presence of an acid acceptor, for example sodium or potassium hydroxide or an excess of the amine.

The amines of formula IV are generally known and if specifically new can be prepared in accordance with the procedures described for preparing the known compounds, e.g. as disclosed in U.S. Pat. Nos. 2,474,818, 2,520,093 and 2,546,658 issued July 5, 1949, Aug. 22, 1950 and Mar. 27, 1951 respectively.

The 2-nitrobenzoyl halides of formula V are likewise members of a generally well known class of compounds.

Alternatively and according to a further process aspect of this invention the 2,1-benzisothiazoles of formula I can be prepared by reacting a 3-chloro-2,1-benzisothiazole having formula III hereinabove with an amine of formula IV at about 50°–150° C. optionally in the presence of a solvent such as N-methyl-2-pyrrolidinone, N,N-dimethylformamide, diethylene glycol monoethyl ether or hexamethylphosphorous triamide.

The 3-chloro-2,1-benzisothiazoles of formula III can be obtained from the generally known o-toluidines of formula VI hereinbelow in accordance with the procedures described by Onaka et al., Itsuu Kenkyusho Nempo 16, 53–63 (1971); Chemical Abstracts 77, 48,320w (1972):

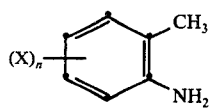

wherein X and $n$ have the previously given meanings.

Alternatively, the 3-chloro-2,1-benzisothiazoles of formula III can be prepared by reacting the corresponding 3-hydroxy compounds with an inorganic acid chloride such as phosphorus oxychloride as described by A. H. Albert et al. J. Heterocyclic Chem. 10, 413 (1973).

When carrying out the above-described procedure to prepare 2,1-benzisothiazoles of formula I wherein $R_2$ is

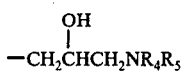

or —Y—NR$_4$R$_5$ in which one of or both R$_4$ and R$_5$ are hydrogen, the requisite diamine intermediate, i.e. R$_1$R$_2$NH wherein R$_2$ is

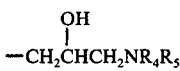

or —Y—NR$_4$R$_5$, (one of or both R$_4$ and R$_5$ being hydrogen), may undergo reaction with a 3-chloro-2,1-benzisothiazole (formula III) at either or both nitrogen atoms to give a mixture of products from which the desired 2,1-benzisothiazole of formula I can be isolated by suitable means known in the art, e.g. high pressure liquid chromatography.

In certain instances the formation of mixtures can be avoided by reacting the 3-chloro-2,1-benzisothiazole with a hydroxy amine, e.g. R$_1$R$_2$NH wherein R$_2$ is —Y—OH followed by conversion of the resulting hydroxy compound to the corresponding chloride, bromide, methanesulfonate or p-toluenesulfonate and then reaction of the latter with an amine R$_4$R$_5$NH to give directly the desired

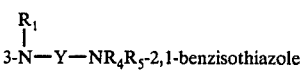

of formula I.

The hydroxy amines, namely $R_1NH-Y-OH$, are generally known and if specifically new can be prepared in accordance with the methods employed in preparing the known compounds.

Due to the presence of the basic amino grouping, the free base forms of the final products represented by formula I and also of the intermediates represented by formula II react with organic and inorganic acids to form acid-addition salts. The compounds of the invention are useful both in the free base form and in the form of acid-addition salts, and both forms are within the purview of the invention. The acid-addition salts are simply a more convenient form for use, and in practice, use of the salt form inherently amounts to use of the base form.

The acid-addition salts are prepared from any organic or inorganic acid. They are obtained in conventional fashion, for instance either by direct mixing of the base with the acid, or, when this is not appropriate, by dissolving either or both the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, dibenzoyltartaric acid, oxalic acid, pyromucic acid, citric acid, lactic acid, mandelic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, cyclohexylsulfamic acid, isethionic acid, methanesulfonic acid, benzenesulfonic acid, p-toluenesulfonic acid, 1,4-naphthalenedisulfonic acid, butylarsonic acid, methane-phosphonic acid, acidic resins, hydrofluoric acid, hydrochloric acid, hydrobromic acid, hydriodic acid, perchloric acid, nitric acid, sulfuric acid, sulfamic acid, glutaric acid, phosphoric acid, arsenic acid, and the like.

All the acid-addition salts are useful as sources of the free base form, by reaction with an inorganic base. It will thus be appreciated that if one or more of the characteristics such as solubility, crystallinity molecular weight, physical appearance, toxicity, or the like of a given base or acid-addition salt thereof render that form unsuitable for the purpose at hand it can be readily converted, in accordance with procedures well known in the art, to another more suitable form.

When the compounds of the invention are to be utilized for pharmaceutical purposes, the acids used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Appropriate medicinally acceptable salts within the scope of the invention are those derived from acids such as hydrochloric acid, acetic acid, lactic acid, tartaric acid, cyclohexylsulfamic acid, methanesulfonic acid, phosphoric acid and the like.

The compounds of this invention have been shown to have useful anti-inflammatory activity as determined by standard pharmacological test procedure carried out on representative examples. Anti-inflammatory activity was determined using (1) the inhibition of carrageenin-induced foot edema test essentially described by Van Arman et al., J. Pharmocol. Exptl. Therap. 150, 328 (1965) as a modification of the procedure of Winter et al., Proc. Soc. Exp. Biol. and Med. 111, 544 (1962) and (2) a modification of the inhibition of adjuvant-induced arthritis test described by Pearson, J. Chronic Diseases 16, 863 (1963) and Glenn et al., Am. J. Vet. Res. 26, 1180 (1965).

In carrying out the method aspect of this invention, i.e. the method of reducing inflammation in mammals which comprises administering to said mammals an effective anti-inflammatory amount of a compound having formula I, said compounds can be administered orally in the form of pills, tablets, capsules, e.g. in admixture with talc, starch, milk sugar or other inert, i.e. non-toxic or pharmacologically acceptable pharmaceutical carrier, or in the form of aqueous solutions, suspensions, encapsulated suspensions, gels, elixirs, aqueous alcoholic solutions, e.g. in admixture with sugar or other sweetening agents, flavorings, colorants, thickeners and other conventional pharmaceutical excipients. When injected subcutaneously, intramuscularly, or intravenously, they can be administered, e.g., as an aqueous or peanut oil solution or suspension using excipients and carriers conventional for this mode of administration. The best route of administration and the best dosage will be apparent from the laboratory tests for activity and toxicity of the selected compound conventionally undertaken as part of the development phase of a pharmaceutical.

The molecular structures of the compounds of the invention were assigned on the basis of the method of their preparation and study of their IR and NMR spectra, and confirmed by the correspondence between calculated and found values for the elemental analyses of representative examples.

The invention is illustrated by the following examples without, however, being limited thereto.

EXAMPLE 1

A. A mixture containing 1200 g. (5.95 moles) of 4-chloro-2-nitrobenzoic acid, 5000 ml. (69 moles) of thionyl chloride and 40 ml. of N,N-dimethylformamide was stirred 4 hours while the temperature was maintained at 26° C. When the evolution of hydrogen chloride subsided, the temperature was raised to 65° C. and stirring was continued an additional hour. After removing excess thionyl chloride by vacuum distillation, the residue was dissolved in 1 l. of 1,2-dichloroethane and the solution was evaporated under reduced pressure. The residue which was essentially free of thionyl chloride was dissolved in 5 l. of 1,2-dichloroethane and the solution was twice treated with decolorizing carbon and filtered to give a final solution of 4-chloro-2-nitrobenzoyl chloride in 1,2-dichloroethane which was used directly in the next step.

B. To a vigorously stirred mixture containing 970 g. (6.2 moles) of freshly distilled $N^1,N^1$-diethyl-1,4-pentanediamine, 4 l. of 1,2-dichloroethane and 1 l. of water at 5°–10° C. there was simultaneously added dropwise a solution containing 5.95 moles of 4-chloro-2-nitrobenzoyl chloride in approximately 8 l. of 1,2-dichloroethane and a solution containing 410g. (6.2 moles) of 85% potassium hydroxide in 1 l. of water. When the addition was complete the ice bath was removed and stirring was continued 0.5 hours at room temperature. The organic layer was separated, dried over anhydrous calcium sulfate and evaporated to dryness under vacuum. The residue was dissolved in 3 l. or 1,2-dichloroethane and the resulting solution was treated with decolorizing carbon and filtered. The filtrate was diluted to 6 l. with additional 1,2-dichloroethane to give a pale yellow solution of 4-choro-N-[4-(diethylamino)-1-methylbutyl]-2-nitrobenzamide which was divided into three equal portions which were used directly in the next step.

In another, similar run an aliquot of the solution was evaporated to dryness under vacuum and the residue converted to the hydrochloride salt with concentrated hydrochloric acid in 2-propanol. Crystallization from 2:1 isopropyl acetate-acetone followed by recrystallization from acetone afforded the hydrochloride, m.p. 130°–132° C.

C. To a stirred, gently refluxing suspension containing 340 g. (1.5 moles) of phosphorus pentasulfide in 14 l. of 1,2-dichloroethane was added dropwise over a period of 2.5 hours 2 l. of a solution containing approximately 2 moles of 4-chloro-N-[4-(diethylamino)-1-methylbutyl]-2-nitrobenzamide in 1,2-dichloroethane. After the addition was complete heating under reflux was continued an additional 4 hours. As the reaction proceeded, a clear, dark-brown solution gradually formed. After standing overnight at room temperature, the mixture was stirred and heated to 50° C., and the excess phosphorus pentasulfide was decomposed by the addition of 570 ml. of water over a period of 0.5 hour. After stirring an additional 0.25 hour at 50° C. the mixture was cooled to 25° C. and made alkaline with 3 l. of 4N aqueous sodium hydroxide. The aqueous layer was separated and extracted with 1,2-dichloroethane. The combined organic portions were washed with water followed by saturated aqueous sodium chloride, dried over anhydrous magnesium sulfate and filtered. The filtrate was combined with the corresponding filtrates produced in two other runs and the solvents were evaporated under vacuum while the temperature was maintained below 50° C. The viscous residue was cooled to 25° C., dissolved in 10 l. of ether and the solution cooled overnight at about 5° C. The slimy precipitate of sulfur which had formed was separated by filtration and the filtrate was concentrated to a volume of about 1 l. The concentrate was diluted with 5 l. of 2-propanol, acidified with 500 ml. of concentrated hydrochloric acid and the solution distilled under vacuum until about 3 l. of distillate had been collected. The suspension which remained was cooled to 25° C. and the solid was collected by filtration, washed successively with cold 2-propanol and acetone and dried under vacuum at 60° C. to give 970 g. of 4-chloro-N-[4-diethylamino)-1-methylbutyl]-2-nitrothiobenzamide hydrochloride as a pale yellow solid, m.p. 173°–176° C. Concentration and cooling the filtrate afforded a second crop of 502 g., m.p. 173°–176° C.

D. To a stirred solution containing 2360 g. (10.5 moles) of stannous chloride octahydrate in 12 l. of concentrated hydrochloric acid at 5° C. was added dropwise over a period of 2 hours a cold solution containing 1470 g. (3.7 moles) of 4-chloro-N-[4-(diethylamino)-1-methylbutyl]-2-nitrothiobenzamide in a mixture of 1180 ml. of water and 6 l. of concentrated hydrochloric acid. Throughout the addition the temperature was not allowed to rise above 10° C. After the addition was complete the mixture was stirred an additional 2.5 hours at room temperature and then cooled to 15° C. The resulting solid was collected by filtration and washed successively with cold, concentrated hydrochloric acid, benzene and ether. The solid was suspended in a mixture of 6 l. of water and 6 l. of toluene. The suspension was cooled and stirred vigorously as it was made alkaline with 4.2 l. of 35% aqueous sodium hydroxide. The temperature was maintained below 35° C. by the addition of crushed ice. The aqueous layer was separated and extracted with toluene. The combined organic portions were washed with water, treated with decolorizing carbon, and concentrated under vacuum to a volume of about 3.5 l. The concentrate was seeded and when crystallization was well established it was diluted gradually with 2 l. of n-hexane. After standing 3 hours at room temperature the solid was collected by filtration. The collected product was slurried thoroughly in 3 l. of cyclohexane and filtered. Washing the solid thus obtained with fresh cyclohexane followed by n-hexane and drying under vacuum at 60° C. afforded 705 g. of 6-chloro-3-[4-(diethylamino)-1-methylbutylamino]-2,1-benzisothiazole, m.p. 112°–115° C. The filtrates and washes were combined, seeded and stirred 2 hours at room temperature to yield an additional 90 g. of product.

Starting with 1030 g. (2.61 moles) of 4-chloro-N-[4-(diethylamino)-1-methylbutyl]-2-nitrothiobenzamide hydrochloride, the above procedure was repeated except that after the addition was complete the reaction mixture was stirred 4.5 hours without cooling; then treated with 150 ml. of n-octanol and stirred overnight at room temperature. The product was isolated as described above to give 715 g. of 6-chloro-3-[4-(diethylamino)-1-methylbutylamino]-2,1-benzisothiazole. A similar run starting with 3,360 g. (8.52 moles) of 4-chloro-N-[4-(diethylamino)-1-methylbutyl]-2-nitrothiobenzamide produced 1,915 g. of product.

E. A stirred solution of 795 g. (2.45 moles) of 6-chloro-3-[4-(diethylamino)-1-methylbutylamino]-2,1-benzisothiazole in 15 l. of absolute ethanol and containing a few seed crystals of the diphosphate salt obtained in a previous run was heated to 67° C. and treated in a steady stream with a solution containing 563 g. (4.9 moles) of 85% phosphoric acid in 1 l. of absolute ethanol. The rate of addition was adjusted to maintain a temperature of 70°–72° C. throughout the addition. Subsequent slow cooling to 65° C. followed by reheating to 71° C. for 0.25 hour and cooling to 15° C. produced a pale yellow crystalline solid which was collected by filtration, washed with absolute ethanol followed by ether and dried under vacuum at 60° C. to give 1273 g. of 6-chloro-3-[4-(diethylamino)-1-methylbutylamino]-2,1-benzisothiazole diphosphate, m.p. 130° C. (dec.).

EXAMPLE 2

A. To a stirred mixture containing 70 g. (0.41 mole) of $N^1,N^1$-diethyl-$N^4$-methyl-1,4-pentanediamine, 800 ml. of dichloromethane, 40 g. of 85% potassium hydroxide and 400 ml. of water at 10° C. was added dropwise a solution containing 0.35 mole of 4-chloro-2-nitrobenzoyl chloride in 300 ml. of dichloromethane. When addition was complete, stirring was continued 1 hour at room temperature. The layers were then separated and the organic portion was washed with water, dried over anhydrous sodium sulfate and evaporated to dryness under vacuum to give 131 g. of 4-chloro-N-[4-(diethylamino)-1-methylbutyl]-N-methyl-2-nitrobenzamide.

B. To a stirred, refluxing mixture containing 100 g. of phosphorus pentasulfide and 5 g. of sodium sulfide nonahydrate in 1.1 l. of 1,2-dichloroethane was added during 0.5 hour a aolution containing 100 g. of 4-chloro-N-[4-(diethylamino)-1-methylbutyl]-N-methyl-2-nitrobenzamide. When addition was complete reflux was continued an additional 3 hours. The reaction mixture was then poured slowly into 250 ml. of water, stirred 0.5 hour, cooled, made alkaline with 2.5 N aqueous sodium hydroxide and extracted with chloroform. The chloroform extracts were washed with water, dried over anhydrous sodium sulfate and evaporated to dryness under vacuum. The residue was triturated with boiling carbon tetrachloride leaving 89 g. of 4-chloro-N-[4-(diethylamino)-1-methylbutyl]-N-methyl-2-nitrothiobenzamide.

C. To a stirred solution containing 83 g. of 4-chloro-N-[4-(diethylamino)-1-methylbutyl]-N-methyl-2-nitrothiobenzamide in 530 ml. of concentrated hydrochloric acid at 15° C. was added a solution containing 150 g. of stannous chloride nonahydrate in 300 ml. of concentrated hydrochloric acid. After stirring 2 hours at room temperature the reaction mixture was cooled and the solid product was collected by filtration. The crude product was partitioned between benzene and 35% aqueous sodium hydroxide. The layers were separated and the aqueous portion was further extracted with benzene. The combined benzene solutions were washed with water, dried over anhydrous sodium sulfate and evaporated to dryness under vacuum. The residue (23.7 g.) was eluted from a column of 600 g. of alumina with 4:1 hexane:ether to separate the product from a polar impurity. Eluted fractions containing the product were combined evaporated to dryness and the residue distilled under vacuum to give 5.1 g. of 6-chloro-3-{[4-(diethylamino)-1-methylbutyl]methylamino}-2,1-benzisothiazole, b.p. 205°–210° C./0.05 mm.

EXAMPLE 3

A. To a stirred mixture containing 29 g. (0.25 mole) of 1-(2-aminoethyl)pyrrolidine, 100 ml. of benzene and 25 ml. of 35% aqueous sodium hydroxide was added dropwise 170 ml. of a solution containing 50 g. (0.25 mole) of 4-chloro-2-nitrobenzoyl chloride in 1,2-dichloroethane. After stirring 1 hour the reaction mixture was extracted with chloroform. The organic layer was washed with water followed by saturated aqueous sodium chloride, dried over anhydrous sodium sulfate and evaporated to dryness under vacuum. The residue was suspended in a mixture of ether and n-hexane, collected by filtration, washed with n-hexane and dried to give 51 g. of 4-chloro-2-nitro-N-[2-(1-pyrrolidinyl)ethyl]benzamide.

B. To a stirred, refluxing suspension of 50 g. of phosphorus pentasulfide in 2 liters of 1,2-dichloroethane was added dropwise a solution containing 51 g. of 4-chloro-2-nitro-N-[2-(1-pyrrolidinyl)ethyl]benzamide in 200 ml. of 1,2-dichloroethane. The mixture was heated 4 hours under reflux. After cooling, the reaction mixture was treated dropwise with 200 ml. of water and the resulting mixture was made alkaline with 10% aqueous sodium carbonate. The layers were separated and the aqueous portion was extracted with chloroform. The combined organic portions were washed with water, dried over anhydrous sodium sulfate and evaporated to dryness under vacuum. The residue was dissolved in 2-propanol and the resulting solution acidified with 20 ml. of concentrated hydrochloric acid. The solution was evaporated under vacuum with gradual replacement of the solvent with fresh 2-propanol followed by isopropyl acetate. The solution was finally evaporated to dryness and the residue cooled 2 days in a refrigerator to afford 28 g. of 4-chloro-2-nitro-N-[2-(1-pyrrolidinyl)ethyl]thiobenzamide hydrochloride.

C. To a cold, stirred solution of 45 g. (0.2 mole) of stannous chloride dihydrate in 200 ml. of concentrated hydrochloric acid containing 0.5 ml. of octanol was added dropwise a solution of 28 g. (0.09 mole) of 4-chloro-2-nitro-N-[2-(1-pyrrolidinyl)ethyl]thiobenzamide hydrochloride in 200 ml. of concentrated hydrochloric acid while the temperature was maintained below 10° C. When addition was complete the reaction mixture was warmed 1 hour at room temperature and then cooled to 5° C. The resulting solid was collected by filtration, washed with concentrated hydrochloric acid followed by benzene and then added to a vigorously stirred mixture of 1 liter of benzene and 200 ml. of 35% aqueous sodium hydroxide. After stirring 1 hour below 10° C. the layers were separated and the aqueous layer was extracted with ethyl acetate followed by 1,2-dichloroethane. The combined organic portions were washed with water, dried over anhydrous sodium sulfate and evaporated to dryness under vacuum. Two recrystallizations from tetrahydrofuran afforded 5.9 g. of 6-chloro-3-{[2-(1-pyrrolidinyl)-ethyl]amino}-2,1-benzisothiazole, m.p. 176°–177° C.

EXAMPLE 4

A. To a stirred mixture containing 60 g. (0.60 mole) of N-methylpiperazine and 50 g. of potassium carbonate in 1 liter of benzene was added dropwise a solution containing 0.50 mole of 4-chloro-2-nitrobenzoyl chloride in 50 ml. of benzene. After addition was complete the reaction mixture was stirred an additional 0.5 hour and then treated with 400 ml. of water. The layers of the resulting biphasic mixture were separated, the organic portion was washed with water followed by saturated aqueous sodium chloride, dried over anhydrous sodium sulfate and concentrated to a volume of 1 liter. The concentrate was diluted with n-hexane. The solid which separated was collected and dried to give 107 g. of 1-(4-chloro-2-nitrobenzoyl)-4-methylpiperazine, m.p. 115°–116° C.

B. To a stirred, refluxing suspension of 50 g. of phosphorus pentasulfide in 3 liters of 1,2-dichloroethane was added dropwise a solution containing 100 g. of 1-(4-chloro-2-nitrobenzoyl)-4-methylpiperazine in 200 ml. of 1,2-dichloroethane. After heating under reflux 2 hours, an additional 25 g. of phosphorus pentasulfide was added and reflux continued an additional 3 hours. The reaction mixture was then cooled, treated slowly with 500 ml. of water and stirred 0.5 hour. The resulting mixture was made alkaline with 250 ml. of 10 percent aqueous potassium carbonate. The aqueous layer was separated and extracted with 1,2-dichloroethane. The combined organic portions were washed with water, dried over anhydrous sodium sulfate and evaporated to dryness. The solid residue was slurried in boiling 2-propanol, collected, washed with ether and dried to give 60 g. of 1-(4-chloro-2-nitrothiobenzoyl)-4-methylpiperazine, m.p. 139°–144° C.

The product of another run was recrystallized twice from 2-propanol to give material with m.p. 142°–144° C.

C. Following a procedure similar to that described in Example 3C but employing 60 g. (0.2 mole) of 1-(4-chloro-2-nitrothiobenzoyl)-4-methylpiperazine and 112 g. (0.5 mole) of stannous chloride dihydrate there was obtained 21.3 g. of 6-chloro-3-(4-methyl-1-piperazinyl)-2,1-benzisothiazole, m.p. 123°–125° C.

EXAMPLE 5

A. Following a procedure similar to that described in Example 4A but employing 52.8 g. (0.6 mole) of N,N-dimethylethylenediamine and 0.5 mole of 4-chloro-2-nitrobenzoyl chloride there was obtained following recrystallization from benzene-hexane 102 g. of 4-chloro-N[2(dimethylamino)ethyl]-2-nitrobenzamide, m.p. 88°–89° C.

B. Following a procedure similar to that described in Example 3B but employing 100 g. (0.36 mole) of 4-chloro-N-[2-(dimethylamino)ethyl]-2-nitrobenzamide and 100 g. of phosphorus pentasulfide there was obtained 68.5 g. of 4-chloro-N-[2-dimethylamino)ethyl]-2-nitrothiobenzamide hydrochloride. Two recrystallizations of a sample from acetonitrile afforded a product having, m.p. 185°–186° C.

C. Following a procedure similar to that described in Example 3C but employing 50 g. (0.16 mole) of 4-chloro-N-[2-(dimethylamino)ethyl]-2-nitrothiobenzamide hydrochloride and 80 g. (0.35 mole) of stannous chloride dihydrate there was obtained 11.6 g. of 6-chloro-2-{[2-(dimethylamino)ethyl]-amino}-2,1-benzisothiazole, m.p. 152°–153° C.

EXAMPLE 6

A. Following a procedure similar to that described in Example 3A but employing 27 g. of 3-(dimethylamino)-propylamine and 50 g. of 4-chloro-2-nitrobenzoyl chloride there was obtained 4-chloro-N-[3-(dimethylamino)-propyl]-2-nitrobenzamide.

B. Following a procedure similar to that described in Example 3B but employing 60 g. of 4-chloro-N-[3-(dimethylamino)propyl]-2-nitrobenzamide and 30 g. of phosphorus pentasulfide there was obtained following trituration with methyl isobutyl ketone and acetonitrile 48 g. of 4-chloro-N-[3-(dimethylamino)propyl]-2-nitrothiobenzamide hydrochloride, m.p. 155°–156° C. Recrystallization of an 8-gram sample from acetonitrile-ethyl acetate afforded 5.3 g., m.p. 156°–157° C.

C. Following a procedure similar to that described in Example 3C but employing 40 g. (0.13 mole) of 4-chloro-N-[3-(dimethylamino)propyl]-2-nitrothiobenzamide and 60 g. (0.26 mole) of stannous chloride dihydrate there was obtained following conversion to the dihydrochloride and two recrystallizations of the latter from 2-methoxyethanol/1,2-dimethoxyethane 7.8 g. of 6-chloro-3-{[3-(dimethylamino)propyl]amino}-2,1-benzisothiazole dihydrochloride, m.p. 225°–236° C.

EXAMPLE 7

A. Following a procedure similar to that described in Example 1B but employing 48 g. (0.41 mole) of 4-(dimethylamino) butylamine and 75 g. (0.37 mole) of 4-chloro-2-nitrobenzoyl chloride there was obtained following two recrystallizations from benzene-hexane 94 g. of 4-chloro-N-[4-(dimethylamino)butyl]-2-nitrobenzamide, m.p. 95°–96° C.

B. Following a procedure similar to that described in Example 3B but employing 80 g. of 4-chloro-N-[4-(dimethylamino)butyl]-2-nitrobenzamide and 40 g. of phosphorus pentasulfide there was obtained 40.6 g. of 4-chloro-N-[4-(dimethylamino)butyl]-2-nitrothiobenzamide. A sample was converted to the hydrochloride and recrystallized twice from 2-propanol to afford a product having m.p. 165°–166° C.

C. Following a procedure similar to that described in Example 3C but employing 40 g. of 4-chloro-N-[4-(dimethylamino)butyl]-2-nitrothiobenzamide and 70 g. of stannous chloride dihydrate there was obtained 6-chloro-3-{[4-(dimethylamino)butyl]amino}-2,1-benzisothiazole which was converted with concentrated hydrochloric acid in 2-propanol to the dihydrochloride monohydrate m.p. 228°–229° C.

EXAMPLE 8

A mixture containing 10.0 g. (0.049 mole) of 3,5-dichloro-2,1-benzisothiazole, 10.0 g. (0.196 mole) of N-methylpiperazine and 50 g. of phenol was stirred and heated under nitrogen at 140° C. overnight. Heating was discontinued and the reaction mixture was poured into 250 ml. of 17.5% aqueous sodium hydroxide. Additional sodium hydroxide was added until the solution remained cloudy. The alkaline mixture was extracted thoroughly with chloroform. The combined extracts were washed with 10% aqueous sodium carbonate, dried over anhydrous sodium sulfate and evaporated to dryness under vacuum. The residue was dissolved in approximately 150 ml. of ethyl acetate. The resulting solution was treated with decolorizing carbon, filtered, concentrated to a total volume of 100 ml. and cooled to −10° C. The precipitated product was collected and washed with cold hexane. Further concentration afforded a second crop. The crops were combined giving 8.23 g. of 5-chloro-3-(4-methyl-1-piperazinyl)-2,1-benzisothiazole, m.p. 84°–88° C.

EXAMPLE 9

A mixture containing 10 g. (0.049 mole) of 3,5-dichloro-2,1-benzisothiazole, 6.55 g. (0.074 mole) of N,N-dimethylethylenediamine and 50 ml. of N-methyl-2-pyrrolidinone was stirred and heated under nitrogen at 70° C. for approximately 24 hours. After standing at room temperature overnight the reaction mixture was poured into 250 ml. of 5% aqueous sodium carbonate and extracted with ether. The combined ethereal extracts were washed with 5% aqueous sodium carbonate, treated with decolorizing carbon, filtered, dried over anhydrous sodium sulfate and evaporated to dryness under vacuum. The residue was dissolved in 100 ml. of boiling ethyl acetate and the hot solution was treated with decolorizing carbon and filtered. The filtrate was concentrated to a volume of 78 ml. and cooled to −10° C. The precipitated product was collected to give 6 g. of 5-chloro-2-{[2-(dimethylamino)ethyl]amino}-2,1-benzisothiazole, m.p. 148°–150° C.

EXAMPLE 10

A mixture containing 16 g. of 3,5-dichloro-2,1-benzisothiazole and 18 g. of freshly distilled $N^1,N^1$-diethyl-1,4-pentanediamine was heated under nitrogen at 110° C. for 24 hours. After cooling, the mixture was poured into isopropyl acetate and extracted with 1N hydrochloric acid. The acidic extracts were made alkaline with 35% aqueous sodium hydroxide and extracted with ethyl acetate. The combined organic extracts were washed with water, dried over anhydrous sodium sulfate and evaporated to dryness under vacuum. The residue was distilled under reduced pressure to give 9.2 g. of 5-chloro-2-{[4-(diethylamino)-1-methylbutyl]amino}-2,1-benzisothiazole, b.p. 203° C./0.5 mm. The latter was dissolved in methanol and treated with a solution containing 5.5 g. of 100% phosphoric acid in methanol. The methanolic solution was diluted with methyl isobutyl ketone and cooled in ice. The resulting precipitate was collected and triturated with ethanol to give 7.3 g. of the diphosphate salt m.p. 185°–187° C.

EXAMPLE 11

A mixture containing 20 g. of 3,6-dichloro-2,1-benzisothiazole and 25 g. of $N^1$-ethyl-$N^1$-(2-hydroxyethyl)-1,4-pentanediamine was heated 5 hours at 128° C. After cooling, the reaction mixture was poured into ice-water and extracted with ethyl acetate. The organic extracts were washed with water, dried over anhydrous sodium sulfate and evaporated to dryness under vacuum. The residue was dissolved in methanol, treated with decolorizing carbon and filtered. To the filtrate was added a solution containing 28 g. of 1,5-naphthalenedisulfonic acid in hot acetonitrile. The mixture was cooled, the supernatant was decanted and the precipitated solid was triturated with 2-propanol-acetonitrile, collected and recrystallized from methanol-acetonitrile to give 33 g. of 6-chloro-3-<{4-[N-ethyl-N-(2-hydroxyethyl)amino]-1-methylbutyl}amino>-2,1-benzisothiazole 1,5-naphthalenedisulfonate, m.p. 153°–155° C. The latter was converted by conventional means to the corresponding dihydrochloride, m.p. 133°–134° C.

EXAMPLE 12

A mixture containing 15 g. of 3,6-dichloro-2,1-benzisothiazole and 20 g. of 3-(diethylamino)-2-hydroxypropylamine was slowly heated with stirring to a temperature of 120° C. at which point the reaction became exothermic and the temperature rose to 140° C. Stirring was continued as the temperature returned to 120° C. and the reaction mixture was then heated at 120° C. for an additional hour. After cooling, the mixture was poured into ice-water, acidified with 6N hydrochloric acid and filtered. The filtrate was washed with ether and then made alkaline with concentrated aqueous ammonia precipitating the product. The solid so-produced was collected, washed with water and recrystallized from ethyl acetate affording 8.5 g. of 6-chloro-3-{[3-(diethylamino)-2-hydroxypropyl]amino}-2,1-benzisothiazole, m.p. 123°–124° C.

EXAMPLE 13

Following a procedure similar to that described in Example 12 but employing 10 g. of 3,6-dichloro-2,1-benzisothiazole and 20 g. of 1-(2-aminoethyl)-4-phenylpiperazine there was obtained 7.8 g. of 6-chloro-3-{[2-(4-phenyl-1-piperazinyl)ethyl]amino}-2,1-benzisothiazole, m.p. 193°–195° C.

EXAMPLE 14

A solution containing 10 g. of 3,5-dichloro-2,1-benzisothiazole and 28 g. of 3-(diethylamino)methyl-4-hydroxyaniline dihydrochloride in 50 ml. of diethylene glycol monoethyl ether and 25 ml. of water was stirred and heated under nitrogen at 100° C. for 8 hours. The reaction mixture was cooled, diluted with water to a volume of 150 ml., acidified with dilute hydrochloric acid and washed with ether. The acidic aqueous solution was brought to pH 8 with aqueous ammonia. The product which precipitated was collected and recrystallized successively from 1,2-dimethoxyethane and ethanol to give 6 g. of 5-chloro-3-{[3-(diethylamino)methyl-4-hydroxyphenyl]amino}-2,1-benzisothiazole, m.p. 203°–205° C.

EXAMPLE 15

Following a procedure similar to that described in Example 14 but employing 10 g. of 3,6-dichloro-2,1-benzisothiazole and 25 g. of 3-(diethylamino)methyl-4-hydroxyaniline dihydrochloride there was obtained following recrystallization from tetrahydrofuran 11 g. of 6-chloro-3-{[3-(diethylamino)methyl-4-hydroxyphenyl]amino}-2,1-benzisothiazole, m.p. 215° C.

EXAMPLE 16

Following a procedure similar to that described in Example 14 but reacting 10 g. of 3-chloro-2,1-benzisothiazole with 21 g. of 3-(diethylamino)methyl-4-hydroxyaniline dihydrochloride in 30 ml. of diglyme and 20 ml. of water there was obtained 3-{[3-(diethylamino)methyl-4-hydroxyphenyl]amino}-2,1-benzisothiazole, m.p. 164°–165° C.

It is contemplated that by following procedures similar to those described hereinabove the following compounds will be obtained.

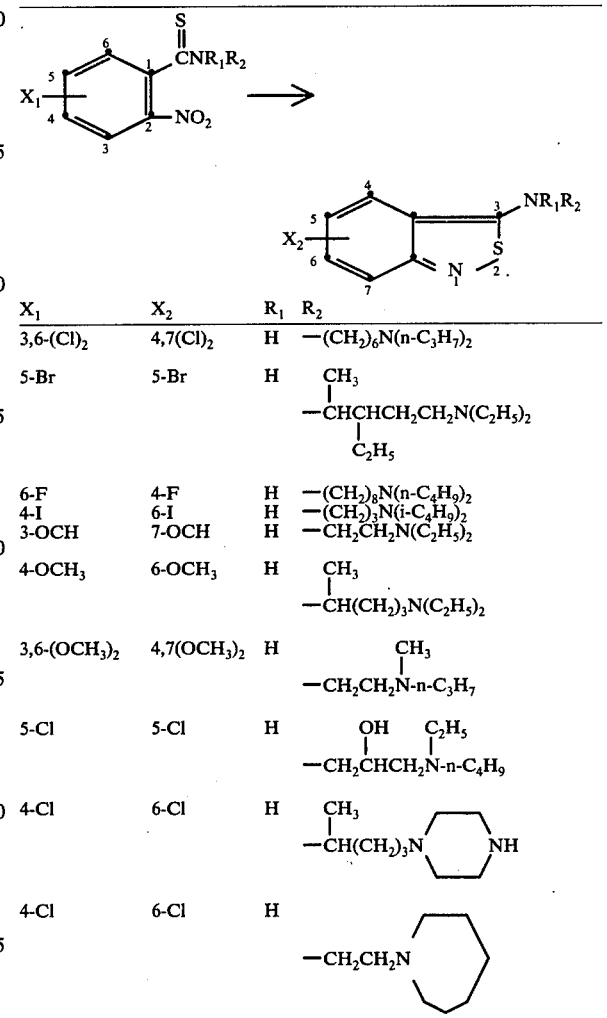

| $X_1$ | $X_2$ | $R_1$ | $R_2$ |
|---|---|---|---|
| 3,6-(Cl)$_2$ | 4,7-(Cl)$_2$ | H | —(CH$_2$)$_6$N(n-C$_3$H$_7$)$_2$ |
| 5-Br | 5-Br | H | —CH(CH$_3$)CH$_2$CH$_2$N(C$_2$H$_5$)$_2$<br>$\quad\quad\quad$C$_2$H$_5$ |
| 6-F | 4-F | H | —(CH$_2$)$_8$N(n-C$_4$H$_9$)$_2$ |
| 4-I | 6-I | H | —(CH$_2$)$_3$N(i-C$_4$H$_9$)$_2$ |
| 3-OCH | 7-OCH | H | —CH$_2$CH$_2$N(C$_2$H$_5$)$_2$ |
| 4-OCH$_3$ | 6-OCH$_3$ | H | —CH(CH$_3$)(CH$_2$)$_3$N(C$_2$H$_5$)$_2$ |
| 3,6-(OCH$_3$)$_2$ | 4,7-(OCH$_3$)$_2$ | H | —CH$_2$CH$_2$N(CH$_3$)-n-C$_3$H$_7$ |
| 5-Cl | 5-Cl | H | —CH$_2$CH(OH)CH$_2$N(C$_2$H$_5$)-n-C$_4$H$_9$ |
| 4-Cl | 6-Cl | H | —CH(CH$_3$)(CH$_2$)$_3$N⟨NH⟩ |
| 4-Cl | 6-Cl | H | —CH$_2$CH$_2$N⟨ ⟩ |

-continued

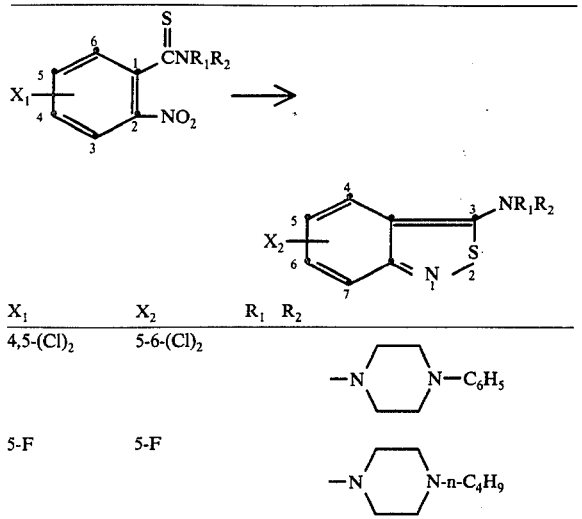

| $X_1$ | $X_2$ | $R_1$ | $R_2$ |
|---|---|---|---|
| 4,5-(Cl)$_2$ | 5-6-(Cl)$_2$ | | -N⟨ ⟩N—C$_6$H$_5$ |
| 5-F | 5-F | | -N⟨ ⟩N-n-C$_4$H$_9$ |

Representative examples of the compounds of this invention have been tested in the carrageenin edema and adjuvant arthritis tests as described hereinabove and found to have anti-inflammatory activity. Test data, given as percent inhibition at a dose expressed in millimoles (mMole/kg) are presented hereinbelow. All test compounds were administered orally.

The data for a number of examples are presented in several separate groups each representing the test results wherein anti-inflammatory activity was measured at one or more dose levels against a single set of controls.

| | Anti-Inflammatory Activity | |
|---|---|---|
| Example | Carrageenin edema (% inhibition mMole/kg) | Adjuvant arthritis (% inhibition mMole/kg) |
| 1B | 29/0.324 | 16/0.324[a] |
| 1C | 38/0.324 | 60/0.324[b] |
| 1D | 19/0.03[a] | 65/0.12 |
| | 14/0.09[a] | |
| | 29/0.27 | |
| 1D | 14/0.02[a] | |
| | 15/0.08[a] | |
| | 47/0.324 | |
| 1D | 0/0.02 | |
| | 24/0.08[a] | |
| | 43/0.324 | |
| 1E | 4/0.03[a] | 27/0.03 |
| | 25/0.09 | 15/0.06[a] |
| | 39/0.27 | 69/0.12 |
| 1E | 30/0.08 | 0/0.03 |
| | 54/0.324 | 24/0.06[a] |
| | | 52/0.12 |
| 1E | 23/0.08[a] | 15/0.06[a] |
| | 34/0.324 | 60/0.12 |
| 1E | 47/0.324 | 23/0.03[a] |
| | | 32/0.06 |
| | | 54/0.12 |
| 1E | 16/0.08[a] | 0/0.03 |
| | 26/0.324[a] | 1/0.06[a] |
| | | 62/0.12 |
| 1E | 28/0.08[a] | 15/0.06[a] |
| | 40/0.324 | 54/0.12 |
| | | toxic/0.24 |
| 1E | 28/0.08 | |
| | 43/0.324 | |
| 1E | 2/0.02[a] | |
| | 15/0.08[a] | |
| | 47/0.324 | |
| 1E | 0/0.02 | |
| | 51/0.08 | |
| | 56/0.324 | |
| 1E | 38/0.324 | |
| | 60/0.64[e] | |
| 2C | 71/0.324 | 0/0.072 |
| | | Toxic/0.324 |
| 3C | 15/0.03[a] | 14/0.324[a] |
| | 12/0.09[a] | |

| | Anti-Inflammatory Activity | |
|---|---|---|
| Example | Carrageenin edema (% inhibition mMole/kg) | Adjuvant arthritis (% inhibition mMole/kg) |
| | 32/0.27 | |
| 3C | 29/0.32 | |
| | 52/0.64 | |
| 4B | 28/0.324 | 0/0.324 |
| 4C | 41/0.324 | 10/0.324[a] |
| 5B | 43/0.324 | 2/0.324[a] |
| 5C | 28/0.324 | 0/0.324 |
| 5C | 19/0.03[a] | |
| | 14/0.09[a] | |
| | 29/0.27 | |
| 6B | 39/0.324 | 8/0.324[a] |
| 6C | 35/0.324 | 0/0.324 |
| 6C | 0/0.03 | |
| | 24/0.09[a] | |
| | 41/0.27 | |
| 7B | 63/1.11[d] | 15/0.80[a] |
| 7C | 0/0.03 | 25/0.324[a] |
| | 9/0.09[a] | |
| | 32/0.27 | |
| 8 | 15/0.08[a] | 0/0.324 |
| | 51/0.324 | |
| 9 | 8/0.08[a] | |
| | 0/0.324 | |
| 9 | 0/0.32 | |
| | 23/0.64 | |
| 10 | 0/0.08 | |
| | 15/0.324[a] | |
| 10 | 62/0.32[e] | |
| | 50/0.64[e] | |
| 11 | 18/0.08 | 36/0.324 |
| | 38/0.324 | |
| 11 | | 54/0.24 |
| | | 67/0.32 |
| | | 71/0.40 |
| 12 | 14/0.08[a] | 16/0.324[a] |
| | 35/0.324 | |
| 13 | 11/0.08[a] | |
| | 16/0.324[a] | |
| 13 | 35/0.064 | |
| 14 | 22/0.08[a] | 0/0.08 |
| | 72/0.324 | |
| 14 | 31/0.08 | |
| | 58/0.324 | |
| 15 | 17/0.08[a] | |
| | 26/0.324[a] | |
| 15 | 0/0.08 | |
| | 0/0.324 | |
| 15 | 21/0.08[a] | |
| | 10/0.324[a] | |
| 15 | 30/0.32 | |
| | 32/0.64 | |
| 16 | 2/0.08[a] | 18/0.324[a] |
| | 55/0.324 | |
| (g) | 21/0.08[a] | 0/0.03 |
| | 7/0.324[a] | 1/0.06[a] |
| (g) | 0/0.02 | 4/0.12[a] |
| | 0/0.08 | 0/0.24 |
| | 27/0.324 | |

[a]not statistically significant
[b]loss of hair, yellow urine
[c]hypothermia
[d]salivation
[e]skeletal muscle relaxation, hypothermia and ptosis at 4 hours post medication.
[f]loss of hair in 4 of 8 animals
(g)3-[4-(diethylamino)-1-methylbutylamino]-2,1-benzisothiazole diphosphate.

Acute oral toxicity was determined for Examples 1E and (g) employing standard toxicological test procedures. The compounds had 7-day $LD_{50}$'s of 1430 and 1730 mg/kg respectively.

We claim:

1. A compound having the formula wherein:
$R_1$ is hydrogen, methyl or ethyl;
$R_2$ is selected from the group consisting of

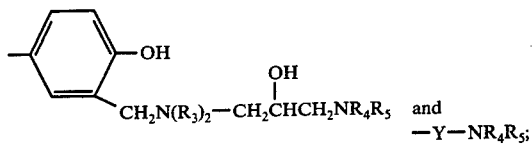

or
R₁ and R₂ taken together with the nitrogen atom are piperazinyl, N-lower alkylpiperazinyl or N-phenylpiperazinyl;

R₃ is methyl or ethyl;

R₄ and R₅ are the same or different and are selected from the group consisting of hydrogen, lower alkyl, hydroxy-lower alkyl, or when taken together with the nitrogen atom, are pyrrolidino, piperidino, hexamethyleneimino, piperazinyl, N-lower alkylpiperazinyl or N-phenylpiperazinyl;

Y is an alkylene group containing from 2 to 8 carbon atoms and separating the two nitrogen atoms by at least 2 carbon atoms;

X occupies any of positions 4,5,6 or 7 and is selected from the group consisting of methoxy and halo; and $n$ is 1 or 2; or 0,1 or 2 when R₂ is

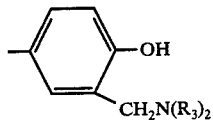

or an acid-addition salt thereof.

2. A compound according to claim 1 wherein R₂ is —Y—NR₄R₅.

3. A compound according to claim 2 wherein R₄ and R₅ taken together with the nitrogen atom are pyrrolidino, piperidino, hexamethyleneimino, piperazinyl, N-lower alkylpiperazinyl or N-phenylpiperazinyl.

4. A compound according to claim 3 wherein X is halo.

5. A compound according to claim 4 wherein X is chloro and $n$ is 1.

6. A compound according to claim 5 wherein Y is an alkylene group containing from 2 to 5 carbon atoms and separating the two nitrogen atoms by at least 2 carbon atoms.

7. A compound according to claim 2 wherein R₄ and R₅ are the same or different and are selected from the group consisting of hydrogen, lower alkyl or hydroxy-lower alkyl.

8. A compound according to claim 7 wherein X is halo.

9. A compound according to claim 8 wherein X is chloro.

10. A compound according to claim 9 wherein Y is an alkylene group containing from 2 to 5 carbon atoms and separating the two nitrogen atoms by at least 2 carbon atoms.

11. A compound according to claim 10 wherein R₄ and R₅ are the same or different and are selected from the group consisting of hydrogen and lower alkyl.

12. A compound according to claim 11 wherein $n$ is 1.

13. 6-Chloro-3-[4-(diethylamino)-1-methylbutylamino]-2,1-benzisothiazole according to claim 12.

14. A compound according to claim 1 wherein R₂ is

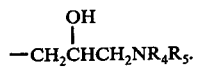

15. A compound according to claim 14 wherein X is halo.

16. A compound according to claim 15 wherein R₄ and R₅ are the same or different and are selected from the group consisting of hydrogen and lower alkyl.

17. A compound according to claim 16 wherein X is chloro and $n$ is 1.

18. A compound according to claim 1 wherein R₂ is

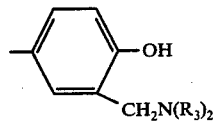

19. A compound according to claim 18 wherein X is halo.

20. A compound according to claim 19 wherein X is chloro and $n$ is 1.

21. A compound according to claim 1 wherein R₁ and R₂ taken together with the nitrogen atom are piperazinyl, N-lower alkylpiperazinyl, or N-phenylpiperazinyl.

22. A compound according to claim 21 wherein X is halo.

23. A compound according to claim 22 wherein X is chloro and $n$ is 1.

24. A pharmaceutical composition for treating inflammation in mammals which comprises from about 25 to 500 mg. of a compound according to claim 1 and a pharmaceutically acceptable carrier.

25. A pharmaceutical composition for treating inflammation in mammals which comprises from about 25 to 500 mg. of a compound according to claim 13 and a pharmaceutically acceptable carrier.

26. A method of reducing inflammation in a mammal in need of such treatment which comprises administering to said mammal an effective anti-inflammatory amount of a compound according to claim 1.

27. A method of reducing inflammation in a mammal in need of such treatment which comprises administering to said mammal an effective anti-inflammatory amount of a compound according to claim 13.

28. A method of reducing inflammation in a mammal in need of such treatment which comprises administering to said mammal an effective anti-inflammatory amount of 3-[4-(diethylamino)-1-methylbutylamino]-2,1-benzisothiazole.

* * * * *

UNITED STATES PATENT AND TRADEMARK OFFICE
CERTIFICATE OF CORRECTION

PATENT NO. : 4,112,105  
DATED : September 5, 1978  
INVENTOR(S) : John Alan Carlson and Malcolm Rice Bell It is certified that error appears in the above-identified patent and that said Letters Patent are hereby corrected as shown below:

On the face page, Abstract, line 1, the comma after -- 1 -- should be deleted.

Column 2, Formula I,

" 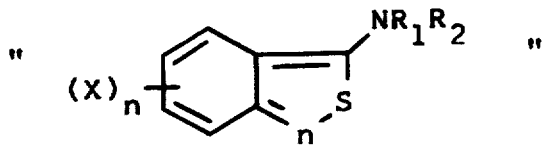 "

should read -- 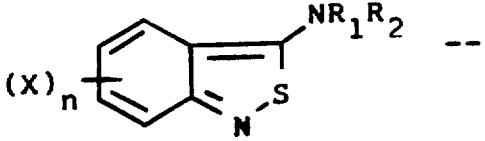 --

UNITED STATES PATENT AND TRADEMARK OFFICE
CERTIFICATE OF CORRECTION

PATENT NO. : 4,112,105

DATED : September 5, 1978

INVENTOR(S) : John Alan Carlson and Malcolm Rice Bell

It is certified that error appears in the above-identified patent and that said Letters Patent are hereby corrected as shown below:

Column 3, line 57, "residues" should read -- resides --.

Column 6, line 13, "hexamethylphosphorous" should read -- hexamethylphosphorus --.

Column 7, line 46, "methane-phosphonic" should read -- methanephosphonic --.

Signed and Sealed this

Sixth Day of November 1979

[SEAL]

Attest:

RUTH C. MASON
Attesting Officer

LUTRELLE F. PARKER
Acting Commissioner of Patents and Trademarks